United States Patent
Dao (10) Patent No.: US 10,428,366 B1
(45) Date of Patent: Oct. 1, 2019

(54) COLLAGENASE ASSAY

(71) Applicant: My Lien Dao, St. Petersburg, FL (US)

(72) Inventor: My Lien Dao, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 68 days.

(21) Appl. No.: 15/210,239

(22) Filed: Jul. 14, 2016

Related U.S. Application Data (63) Continuation-in-part of application No. 14/753,799, filed on Jun. 29, 2015, now abandoned.

(60) Provisional application No. 62/020,179, filed on Jul. 2, 2014.

(51) Int. Cl.
| | | |
|---|---|---|
| A61K 38/39 | (2006.01) | |
| C12Q 1/37 | (2006.01) | |
| G01N 1/30 | (2006.01) | |

(52) U.S. Cl.
CPC ........ *C12Q 1/37* (2013.01); *C12Y 304/24003* (2013.01); *G01N 1/30* (2013.01); *G01N 2001/302* (2013.01); *G01N 2333/78* (2013.01); *G01N 2333/96494* (2013.01)

(58) Field of Classification Search
CPC .. H04L 5/003; H04W 28/18; H04W 72/0446; C12Q 1/40; C12Y 302/01; C12Y 302/01004; C12Y 302/01022; C12Y 302/01025; C12Y 302/01055; D21H 11/18; D21H 11/20; G01N 2333/924; G01N 2333/94; G01N 2333/942; G01N 30/64; G01N 30/7233; G01N 30/96; G01N 33/34; G01N 33/343
See application file for complete search history.

(56) References Cited

U.S. PATENT DOCUMENTS

| | | | |
|---|---|---|---|
| 4,023,933 A | 5/1977 | Bradford et al. | |
| 4,176,009 A | 11/1979 | Sakakibara et al. | |
| 4,219,337 A | 8/1980 | Grossberg et al. | |
| 4,931,386 A * | 6/1990 | Silver | C12Q 1/37 435/23 |
| 6,057,160 A | 5/2000 | Silber et al. | |
| 2011/0207671 A1* | 8/2011 | Chang | A61L 27/24 514/17.2 |

FOREIGN PATENT DOCUMENTS

| | | |
|---|---|---|
| EP | 0319334 A2 | 6/1989 |
| EP | 1039299 B1 | 9/2000 |
| EP | 2016421 B1 | 1/2009 |

OTHER PUBLICATIONS

Welgus et al. (1980) J. Biol. Chem. 255(14): 6806-6813. (Year: 1980).*
McPherson et al. (1986) Journal of Biomedical Materials Research 20: 79-92. (Year: 1986).*
Subrahmanyam et al. (2003) Indian Journal of Clinical Biochemistry 18(1): 5-7. (Year: 2003).*
Collagenase. Worthington Biochemical Company. I.U.B. 3.4.24.3, C.A.S. 9001-12-1. Date Accessed Aug. 19, 2015. http://www.worthington-biochem.com/cls/default.html.
Material Safety Data Sheet: Aniline blue MSDS. ScienceLab.com: Chemical & Laboratory Equipment. Date Accessed: Aug. 19, 2015. http://www.sciencelab.com/msds.php?msdsId=9922942.
Material Safety Data Sheet: Brilliant blue R-250 MSDS. ScienceLab.com: Chemical & Laboratory Equipment. Date Accessed: Aug. 19, 2015. http://www.sciencelab.com/msds.php?msdsId=9925778.
Aznavorian et al., Membrane Type I-Matrix Metalloproteinase-Mediated Degradation of Type I Collagen by Oral Squamous Cell Carcinoma Cells. Cancer Research. 2001. vol. 61: 6264-6275.
Burokerkilgore et al. A Coomassie Brilliant Blue G-250-Based Colorimetric Assay for Measuring Activity of Calpain and Other Proteases. Analytical Biochemistry. vol. 208, Issue 2, Feb. 1, 1993, pp. 387-392; and.
Nethery et al., A spectrophotometric collagenase assay. 1986. Anal Biochem. vol. 159: 390-395.
Sedmak et al., A rapid, sensitive, and versatile assay for protein using Coomassie brilliant blue G250. Analytical Biochemistry. 1977. vol. 79: 544-552.
Teratoa et al., A rapid assay method of collagenase activity using 14C-labeled soluble collagen as substrate. Biochimica et Biophysica Acta 1976. vol. 445: 753-762.

* cited by examiner

*Primary Examiner* — Lisa J Hobbs
(74) *Attorney, Agent, or Firm* — Javier M. Mixco; Nilay J. Choksi; Smith & Hopen, P.A.

(57) ABSTRACT

A method of measuring soluble or insoluble cell or tissue-associated collagenase activity. The substrate includes native collagen fibrils that were stained with COOMASSIE Brilliant Blue R-250. Incubation with collagenase can be observed in real-time by the generation of digested smaller fragments. The degraded blue fragments are obtained by filtration through class fibers, onto which intact collagen fibrils are retained. The filtrate containing the blue collagen fragments is incubated with a detergent in order to extract the blue dye, and the mixture is centrifuged in order to separate the dye in the supernatant from the pellet, which contains de-stained collagen fragments and other insoluble materials contained in the test samples (such as bacterial cells or tissues). The amount of dye extracted is quantified by measuring the amount of dye extracted from these fragments, i.e., the absorbance at 600 nm using a spectrophotometer or an ELISA reader.

19 Claims, 5 Drawing Sheets

COLLAGENASE ASSAY

CROSS-REFERENCE TO RELATED APPLICATIONS

This nonprovisional application is a continuation-in-part of and claims priority to U.S. Nonprovisional patent application Ser. No. 14/753,799, entitled "Blue Collagenase Assay", filed Jun. 29, 2015 by the same inventor, which claims priority to U.S. Provisional Patent Application No. 62/020,179, entitled "Blue Collagenase Assay", filed Jul. 2, 2014, by the same inventor, both of which are incorporated herein by reference in their entireties.

BACKGROUND OF THE INVENTION

1. Field of the Invention

This invention relates, generally, to collagenases. More specifically, it relates to blue collagenase assays.

2. Brief Description of the Prior Art

Collagenases are defined as proteases that can digest native collagen in the triple helix region. There is no spectrophotometric assay that uses native collagen fibrils ["Collagenase", Worthington Biochemical Company, I.U.B. 3.4.24.3, C.A.S. 9001-12-1]. Commonly used substrates in collagenase assay kits include synthetic peptides, or denatured collagen such as acid soluble collagen and heat-gelling collagen or gelatin. Since denatured collagen can also be degraded by gelatinase and/or protease such as trypsin, assays based on the digestion of these substrates are not specific for the determination of collagenase activity, and hence are referred to by those of ordinary skill in the art as collagenolytic activity, which can be broadly defined as just the ability to lyse collagen, gelatin, and other proteins containing proline.

Collagen can be stained in blue tissue section by blue dyes such as aniline blue dyes (e.g., MSDS: CI#: 42755; Synonym: Acid blue 22 China blue; Chemical Name: Not available; Chemical Formula: $C_{32}H_{27}N_3O_9S_3 \cdot 2Na$) and COOMASSIE Brilliant Blue R-250 (MSDS: CI#: 42660; Synonym: Acid Blue 83; Acid Brilliant Blue; CI Acid Blue 83; Chemical Name: Benzenemethanaminium, N-[4-[[4-[(4-ethoxyphenyl)amino]phenyl][4-[ethyl [(3-sulfophenyl) methyl]amino]phenyl]methylene]-2,5-cyclohexadien-1-ylidene]-ethyl-3-sulfo-, inner salt, monosodium salt; Chemical Formula: $C_{46}H_{44}N_3O_7S_2 \cdot Na$). This property has been applied to the preparation of blue collagen-coated plastic plates (gelled collagen and dried onto plastic plates) for the observation of collagen degradation assay by oral squamous carcinoma cells in cancer research (Aznavorian et al., Cancer Research, American Association for Cancer Research, 2001:61:6264-6275), and adapted to spectrophotometric measurement of the plates (Nethery et al., "A spectrophotometric collagenase assay", 1986, Anal Biochem 159(2):390-5). Since the collagen is denatured in the heat-gelling process, the use of inhibitors of other enzymes is applied in order to deduce that the activity observed is that of collagenase (Aznavorian et al., Cancer Research, American Association for Cancer Research, 2001:61:6264-6275).

The interest in the detection and measurement of collagenase activity and/or use of COOMASSIE dye has generated the publication of numerous assays. Examples include U.S. Pat. Nos. 4,023,933; 4,176,009; 4,219,337; 6,057,160; EP 0319334 A2; EP 1039299 BI; EP 2016421 BI; Sedmak et al. A rapid, sensitive, and versatile assay for protein using Coomassie brilliant blue G250. Analytical Biochemistry. Volume 79, Issues 1-2, 1 May 1977, pp. 544-552; Burokerkilgore et al. A Coomassie Brilliant Blue G-250-Based Colorimetric Assay for Measuring Activity of Calpain and Other Proteases. Analytical Biochemistry. Volume 208, Issue 2, 1 Feb. 1993, pp. 387-392; and Teratoa et al. A rapid assay method of collagenase activity using 14C-labeled soluble collagen as substrate. Biochimica et Biophysica Acta (BBA)—Enzymology. Volume 445, Issue 3, 11 Oct. 1976, pp. 753-762. However, each of these references has their own respective drawbacks and would be incapable, individually or in combination, of measuring soluble or insoluble cell or tissue-associated collagenase activity using COOMASSIE dye.

Accordingly, what is needed is an improved assay, kit, and/or vessel for detection of activity of blue collagenase. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved collagenase assay is now met by a new, useful, and nonobvious invention.

In an embodiment, the current invention is a method of measuring true collagenase activity in a sample, such as bacteria or a biological sample. The collagenase may include soluble collagenase, insoluble cell-associated collagenase, or insoluble tissue-associated collagenase. The method includes staining native, optionally insoluble, collagen fibrils with a dye at saturation level, where the collagen fibrils are dried or lyophilized and the dye can stably stain the fibrils. In typical cases, the fibrils are not solubilized by acid or gelled by heat. The dyed fibrils are suspended in a collagenase substrate buffer (e.g., Tris, NaCl, and $CaCl_2$; a phosphate buffer of NaCl, KCl, $Na_2HPO_4$, and $KH_2PO_4$ in deionized water) and optionally sodium azide, and this suspension is incubated at about 37° C. on a rotator. The presence of collagenase activity results in digestion of the dyed collagen fibrils into smaller, dyed collagen particulates that can be readily observed in the resulting mixture. The mixture is filtered (e.g., through glass wool which would retain any undigested collagen fibrils), and the particulates are collected in the resulting filtrate. The dye is extracted from the dyed collagen particulates by adding an organic solvent (e.g., formamide) or detergent (e.g. polysorbate 20) to the filtrate, followed by incubation overnight at 37° C. on a rotator, or for 2 hours at 65° C. in a water bath. The blue dye is separated from the colorless particulates in the filtrate by centrifugation at 10,000×g for 5 min, and the absorbance at 600 nm of the supernatant is measured by using a plate reader or a spectrophotometer at an optimal wave length of about 600 nm.

The collagen fibrils were sized down by cutting or by using a blender at grinding/chopping setting, passed through a 1 mm sieve and collected as dry collagen.

The dye may be a triphenylmethane dye, such as COO-MASSIE Brilliant Blue R-250, having a chemical structure as follows:

In this case, the collagen fibrils can be stained using this dye in a solution of acid-methanol-water that comprises of 10% acetic acid, and 40% methanol in double-distilled water (10:40:50, v:v:v), at a ratio of 500 mg collagen in about 20-30 ml of the dye solution.

Collagenase activity may be quantified by a concentration of the extracted dye. This concentration is proportional to a concentration of the collagen particulates released. A quantification of the collagenase may, in turn, be used to detect and quantify true collagenase activity in invasive pathogenic bacteria for development of drugs or vaccines to prevent invasive bacterial disease by blocking collagenase activity.

The dyed collagen fibrils may be incubated with trypsin to ensure that the dyed collagen fibrils are resistant to trypsin, and hence are a specific substrate for collagenase.

In a separate embodiment, the current invention can include any one or more, or even all, of the foregoing characteristics and features.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

The dark blue dot represents the average OD600 nm of the blue dye extracted from the collagen fragments digested by Sm GS5 collagenase.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In an embodiment, the current invention is a Blue Collagenase Assay and/or a methodology to quantitatively and qualitatively measure and analyze soluble or insoluble cell or tissue-associated true collagenase activity in bacteria and biological samples using dye (e.g., triphenylmethane dye, COOMASSIE Brilliant Blue)-stained collagens as a substrate for the collagenase. Unlike current collagenase assays that use acid-solubilized or heat-gelled collagen, or synthetic peptides as substrates, the Blue Collagenase Assay uses dye (e.g., triphenylmethane dye such as COOMASSIE Brilliant Blue R-250)-stained collagen fibrils. Incubation of a test sample containing collagenase with the blue collagen fibrils showed the generation of digested blue collagen fragments, which can be observed in real-time, and isolated by filtration through glass wool, which retains the undigested collagen fibrils. Collagenase activity is quantified by the concentration of the blue dye extracted from these fragments, which is proportional to the concentration of collagen fragments released.

Blue collagenase assay is a method of measuring soluble or insoluble cell or tissue-associated collagenase activity. The substrate includes native fibrillar collagen fragments that were stained with a triphenylmethane dye (e.g., COOMASSIE Brilliant Blue), which can stably stain the insoluble collagen fibrils. Incubation with collagenase can be observed in real-time by the generation of digested smaller fragments, and can be obtained by filtration, and can be quantitated by measuring the amount of dye extracted from these fragments.

The present method is amenable to the preparation of a Blue Collagenase Assay kit, which would contain reaction tubes containing blue collagen substrate, pipet tips plugged with glass wool for filtration, collection tubes containing the extraction solution, and a bottle of concentrated substrate buffer.

In an embodiment, the current invention is a method to assay for collagenase using lyophilized collagen fibrils (e.g., Type I), from bovine Achilles tendon that can be obtained commercially (for example SIGMA-ALDRICH, Product No. C9879) or prepared according to the method of Einbinder, J. et al. (J. Biol. Chem., 188, 335 (1951).

This method allows for both the qualitative observation of collagenase activity and the quantitative activity assay using a spectrophotometer. It is contemplated and shown herein that this method is applicable to both soluble and cell-associated collagenase.

In certain embodiments, the method presented herein is unique in staining lyophilized or dried collagen with COOMASSIE Brilliant Blue R-250 (though other dyes are contemplated herein as well) at saturation level and in its native state without being solubilized by acid and/or gelled by heat. Incubation of a test sample containing collagenase with the blue collagen results in the digestion of the blue collagen into smaller fragments that can be collected by filtration through glass wool, which retains the undigested collagen fibrils. The dye can be extracted from the digested blue fragments by the addition of the detergent polysorbate 20 (TWEEN 20) or other organic solvent (e.g., formamide), separated from the particulate by centrifugation, and quantified by spectrophotometric measurement of the absorbance at the optimal wavelength of 600 nn. The concentration of the blue dye is proportional to the concentration of digested blue polypeptide fragments. By using the present dye extraction method, it is possible to assay both soluble collagenase (e.g., *Clostridium histolyticum* collagenase) and insoluble tissue or cell-associated collagenase (e.g., *Streptococcus mutans* cell-associated collagenase). In certain embodiments, this assay can be used to detect and quantify true collagenase activity in invasive pathogenic bacteria for the development of drugs or vaccine to prevent invasive bacterial disease (IBD) by blocking collagenase activity.

In application, the present method can be applied to the staining other insoluble proteins, such as gelatin granules and other types of collagen for use as a substrate for the analysis of gelatinase and other collagenase types. The present method can also be used to analyze metalloproteinases in humans and animals.

Example 1

1. Staining of Collagen

Bovine Achilles tendon type I collagen fibrils were obtained from Sigma-Aldrich or prepared according to the method of Einbinder, J. et al., Binding of mucopolysaccharides and dyes by collagen (J. Biol. Chem., 188, 335, 1951). Collagen fibrils were air-dried or lyophilized, and then cut into shorter pieces using any suitable methodology, for example hand-cutting with scissors or by using a blender at "grinding/chopping" setting. The fibrils were passed through a 1 mm sieve and collected as dry collagen.

The dry collagen was mixed with about 0.1%-0.2% COOMASSIE Brilliant Blue in a solution of about 10% acetic acid, about 40% methanol in 50% double-distilled water (standard method for staining protein bands in polyacrylamide gel), at a ratio of 500 mg collagen in 20-30 ml of dye in acetic acid-methanol-water solution, in a conical centrifuge tube on a rotator for around 3-5 min at room temperature when all the collagen fibrils were saturated with the blue dye, after which time phosphate buffered saline, pH 7.5 (PBS) was added up to 50 ml (PBS: 80 g NaCl, 0.2 g KCl, 1.44 g $Na_2HPO_4$, 0.24 g $KH_2PO_4$ in 1 L double distilled water, pH 7.5 as described in Cold Spring Harbor Protocols).

The blue collagen suspension was centrifuged at 1500×g for 2 minutes, and the supernatant was discarded. The excess dye was removed by rinsing with the solution of acetic acid-methanol-water (1:4:5, v:v:v).

The blue collagen was extensively washed with PBS by mixing and letting the collagen fibrils sediment to the bottom of the tube (or by centrifugation at 500×g for 2 min), and pouring off the upper phase that contained the excess dye and floating blue collagen particles until the supernatant came out clear and free of floating particles.

The blue collagen was rinsed in 30 ml of a solution of acetic acid-methanol-water (1:4:5, v:v:v), followed by centrifugation (1500×g for 2 min), and three washes with CSB containing sodium azide added at 0.02% with centrifugation in between. The blue collagen was finally re-suspended in CSB containing sodium azide added at 0.02%.

Aliquots of the blue collagen suspension (250 µl) were distributed into graduated 2 ml microcentrifuge tubes (FISHER SCIENTIFIC Co.) using 1 ml pipettor and a cut-off pipet tip to pipet up the collagen fibrils. The filled microcentrifuge tubes were stored in the refrigerator until used. The blue collagen suspension is stable, even when stored at room temperature (25° C.). Alternatively, the blue collagen can be lyophilized.

Quality control for collagenase substrate specificity can be performed by incubation of the dyed collagen fibrils with Trypsin. This enzyme can digest denatured collagen and gelatin, but not native collagen fibrils.

Example 2

As an example, application of the blue collagenase assay to soluble *Clostridium histolyticum* collagenase (see FIGS. 2 and 4A) and cell-associated *Streptococcus mutans* collagenase (see FIGS. 3A-3C and 4B) is described herein.

The method generally includes the following steps:
1. The collagen fibrils are stained using COOMASSIE Brilliant Blue R-250 (C46-H44-N3-07-S2-Na) or other suitable dye.
2. The blue collagen fibrils are suspended in collagenase substrate buffer (50 mM Tris, 50 mM NaCl, 10 mM $CaCl_2$, pH 7.5), with sodium azide added at 0.02%.
3. The blue collagen fibrils in suspension are incubated with the test sample at 37° C. on a rotator (see FIG. 3A).
4. The collagenase activity results in the production of blue collagen particulates that can be readily observed.
5. After the incubation time of three (3) hours or longer, the mixture is filtered through glass wool/fibers to which the blue collagen fibrils are retained, and the small blue fragments are collected in the filtrate (see FIGS. 3B-3C).
6. To determine the amount of digested collagen, the blue dye is extracted by incubation of the filtrate in the presence of polysorbate 20 (TWEEN 20) added at 2%, at 37° C. on a rotator.
7. The mixture, containing the blue dye, is centrifuged at 12,000×g for 5 minutes.
8. Absorbance of the blue supernatant is measured at 600 nm using a spectrophotometer or ELISA reader.

2. Establishment of a Standard Curve Using Soluble *C. histolyticum* Collagenase of Known Enzymatic Activity

*C. histolyticum* collagenase of known enzymatic activity (SIGMA-ALDRICH No. C0130, Lot# SLBM8384V) was assayed at the following concentrations: 25 U/ml, 50 U/ml, 75 U/ml, and 100 U/ml.

The reaction mixture (2 ml) consisted of 250 µl of blue collagen suspension in 1 ml Collagenase substrate buffer (CSB) and each ChC sample was diluted in CSB up to 1 ml. Each ChC concentration sample was assayed in quadruplicates. Incubation was for 4 h at 37° C. on a rotator.

Essentially, up to 1.75 ml of test sample can be used and added to each tube containing 250 µl of dyed collagen (total volume of the reaction mix is 2 ml).

The tubes were incubated at 37° C. on a rotator for 4 hours. Digestion of the blue collagen by collagenase was periodically observed, and the generation of small blue collagen particles appeared to be dose-dependent. At the end of the incubation period, the reaction mixture from each tube was filtered through loosely packed glass wool.

After the incubation period, the reaction mixture was poured into 1 ml pipet tip containing loosely packed glass fibers, and the filtrate containing small blue collagen fragments were collected into a fresh 2 ml-microcentrifuge tube containing 200 µl of 20% polysorbate 20 (TWEEN 20) in substrate buffer.

The blue dye was then extracted from the blue collagen by incubation at 65° C. in a water bath for about 2-3 hours until the blue dye is completely extracted from the digested collagen fragments.

After the extraction period, the tubes were centrifuged at 10,000×g for 5 minutes to sediment the de-stained collagen fragments and other insoluble components in the test samples. The supernatant containing the dye from each tube was measured for the absorbance at 600 nm using a spectrophotometer or an ELISA reader. Tubes incubated with buffer alone (1 ml substrate buffer containing 2% polysorbate 20 (TWEEN 20) were used as a blank.

Figure 1A:
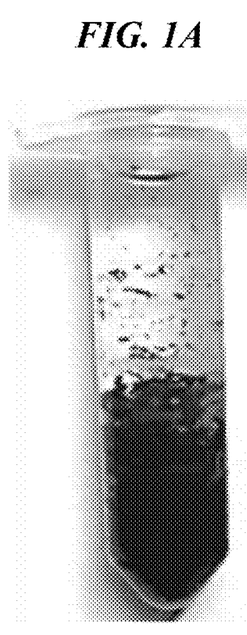
FIG. 1A depicts a collagen suspension incubated with trypsin.
Figure 1B:
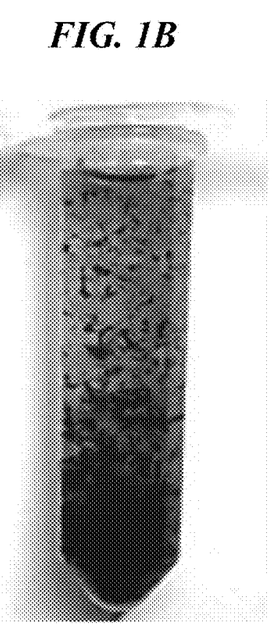
FIG. 1B depicts a collagen suspension incubated with C. histolyticum collagenase. Only C. histolyticum collagenase could digest the dyed collagen fibrils.
Figure 2:
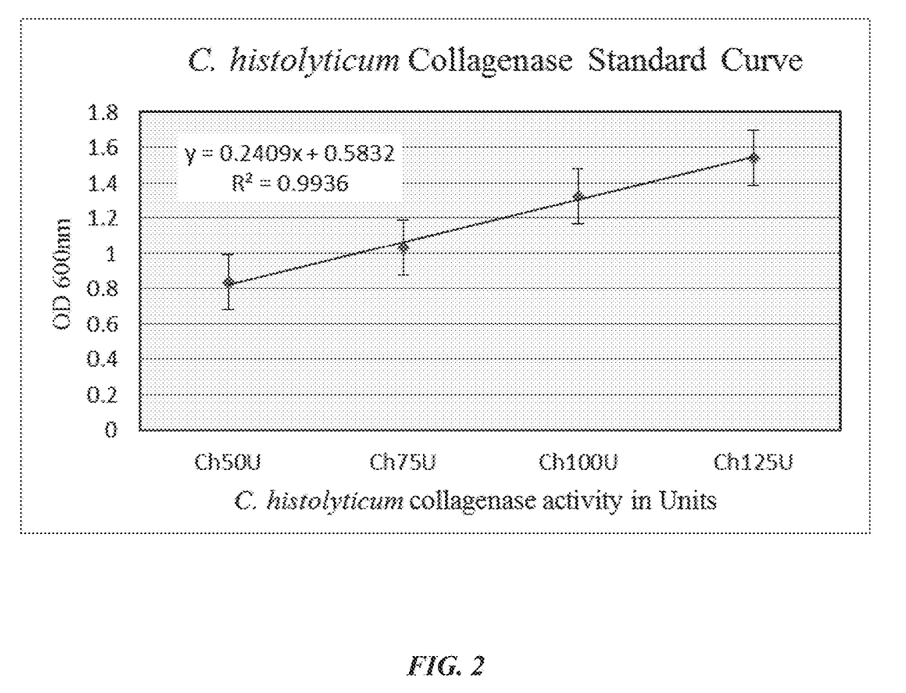
FIG. 2 is a C. histolyticum collagenase standard curve. Ch collagenase was assayed at four concentrations: Ch50U, Ch75U, Ch100U, and Ch125U (medium range). A high correlation between Ch collagenase activity in units and the absorbance at 600 nm of the blue dye extracted from the digested fragments was observed.
Figure 3A:
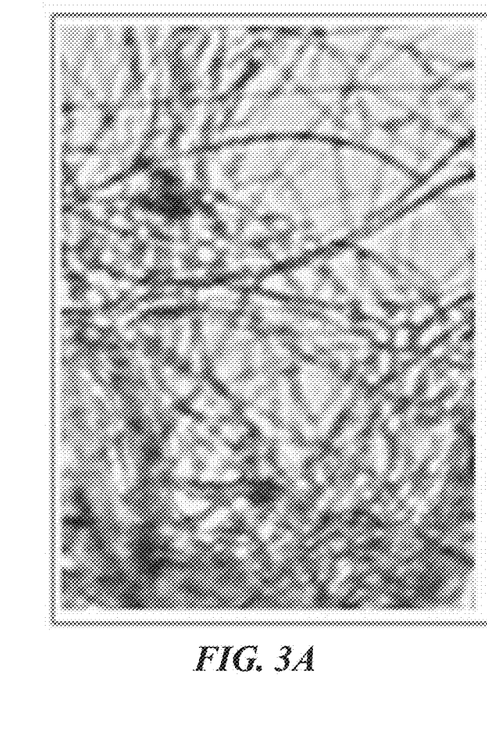
FIG. 3A is a micrograph (×400 magnification and ×3.1 digital zoom) undigested collagen fibrils.
Figure 3B:
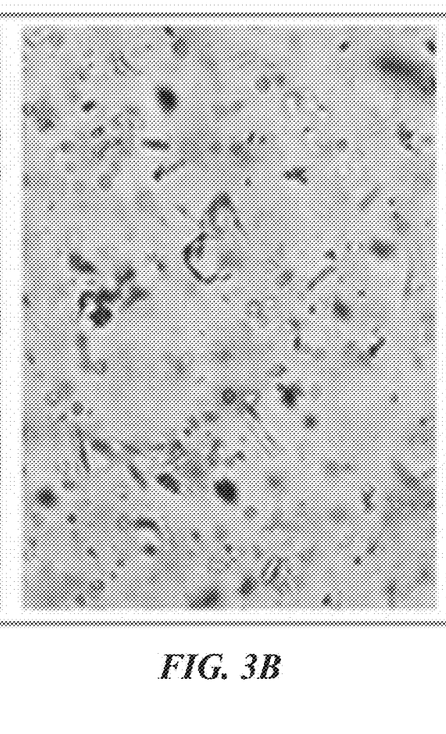
FIG. 3B is a micrograph (×400 magnification) depicting filtrate containing digested collagen fragments and S. mutans.
Figure 3C:
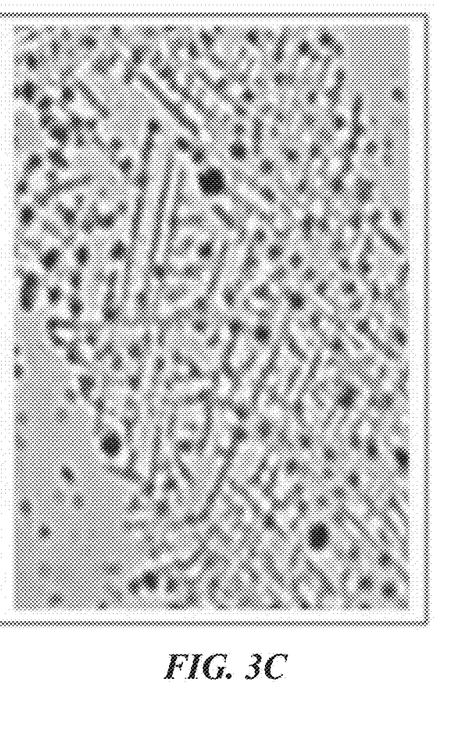
FIG. 3C is a micrograph (×400 magnification and ×3.1 digital zoom) depicting clumped digested collagen fragments and S. mutans in a sample of filtrate that was dried onto a glass slide after application of a drop of lysate.

A standard curve was established with *C. histolyticum* collagenase (U/ml versus OD at 600 nm) as shown in FIG. 2.

As a side note, due to the heterogeneity of the collagen fibrils, a standard curve typically was established for each lot of blue collagen. For the same reason, samples were assayed in quadruplicates so that occasional outliers could be rejected without interfering with statistical analysis.

Depending on the amount of enzyme in the test samples, a standard curve can be established with *C. histolyticum* collagenase at various concentrations: 5U-25 U/ml (at low range); 50-125 U/ml (at medium range) and up to 300 U/ml (at higher range). A quick test can be performed with *C. histolyticum* collagenase and the test samples in order to determine the appropriate range of the concentrations needed for the standard curve. This is facilitated by the observation of collagen degradation in real-time.

Figure 4A:
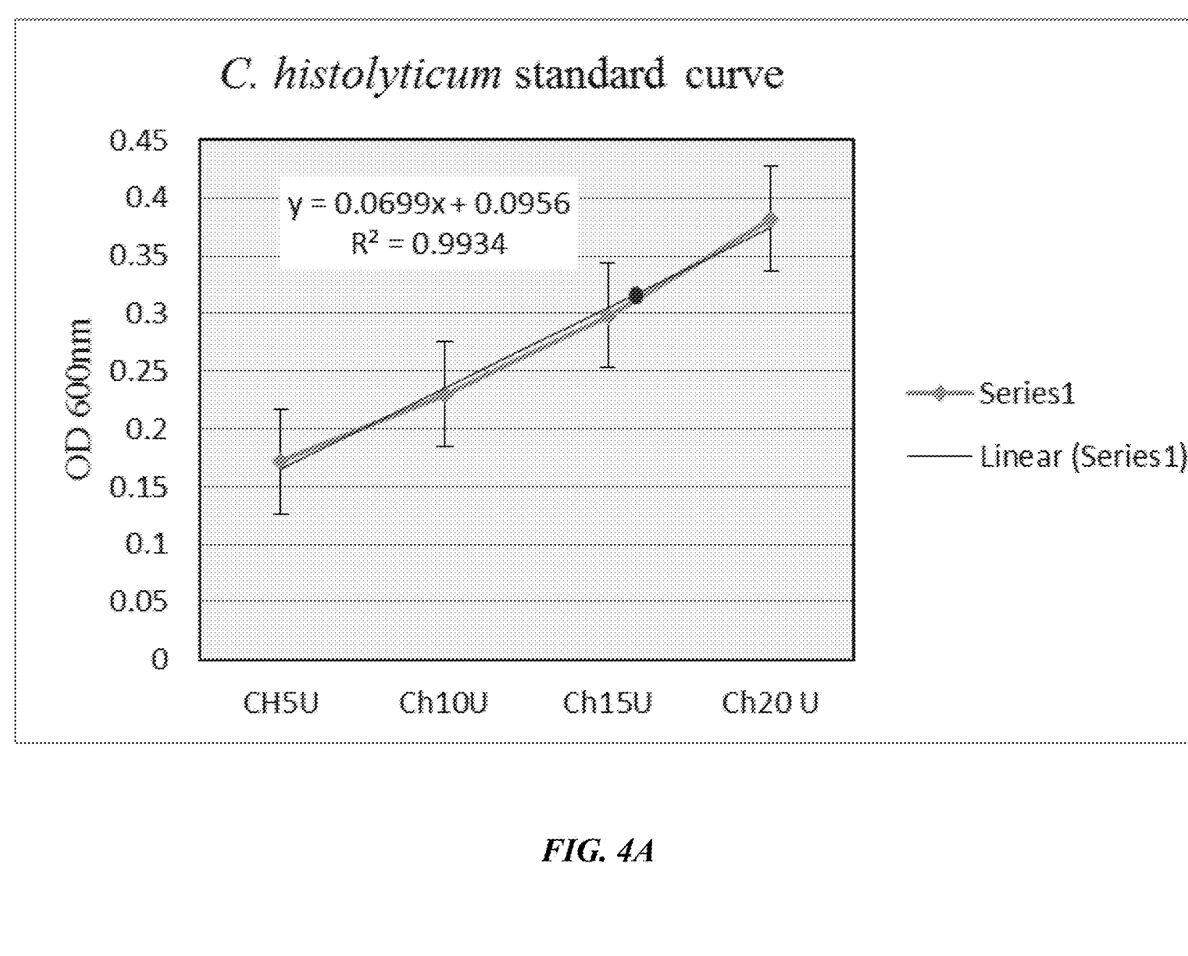
FIG. 4A is a C. histolyticum standard curve for use in the analysis of collagenase in Sm GS5. Ch collagenase was assayed at four concentrations: Ch5U, Ch10, Ch15U, and Ch20U (low range). A high correlation between Ch collagenase activity in units and the absorbance at 600 nm of the blue dye extracted from the digested fragments was observed.
Figure 4B:
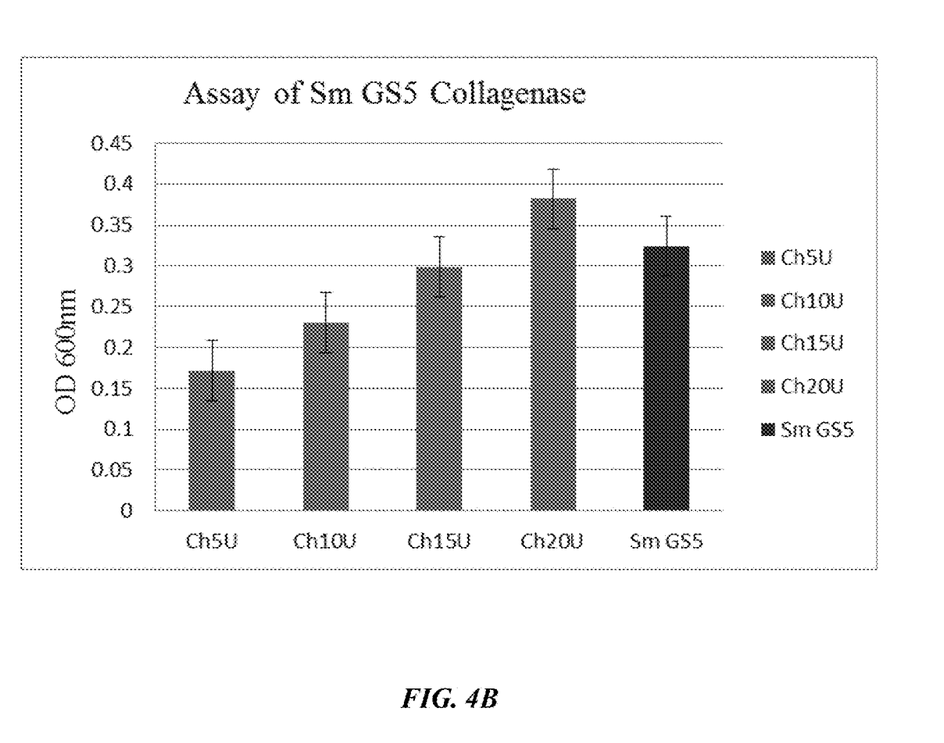
FIG. 4B depicts collagenase activity in S. mutans. S. mutans GS5 was cultured to saturation level, and the bacterial cells were suspended in collagenase substrate buffer at a concentration of 2.5 $OD_{600\ nm}$ per ml. Four tubes of bacterial cell suspension were freeze-thawed 3× and assayed in parallel with quadruplicate samples of C. histolyticum collagenase at four different concentrations: Ch5U, Ch10U, Ch15U, and Ch20U). Sm GS5 collagenase activity was derived from the C. histolyticum standard curve of FIG. 4A: Around 16.75 ChC.eqU were observed in 2.5 OD of Sm cells (corresponding to 6.467 ChC.eqU per 1 OD Sm cells).

The calculated coefficient of correlation of ChC U with the absorbance at 600 nm is significant (see FIGS. 2, 4A, and 4B, with $R^2 > 0.99$).

3. Activity Assay of Bacterial Cell-Associated Collagenase

*Streptococcus mutans* whole cells were used as a model of insoluble collagenase.

Bacterial cells in saturated cultures were collected by centrifugation at 3220×g for 20 minutes, and the cell pellet was suspended in substrate buffer at a concentration of 2.5 $OD_{600\,nm}$ per ml.

One ml-aliquot of bacterial cell suspension was freeze-thawed three times to expose the membrane-associated collagenase and then added to each tube containing 250 µl of blue collagen substrate, and substrate buffer was added up to 2 ml. The assay was performed in quadruplicate.

*C. histolyticum* collagenase with known enzyme activity (SIGMA-ALDRICH No. C0130, Lot# SLBM8384V) and the Sm samples to be tested were analyzed in parallel. *C. histolyticum* collagenase was selected as a test sample for the establishment of a standard curve. *C. histolyticum* collagenase Type I of known enzyme activity (SIGMA-ALDRICH) was solubilized in substrate buffer at 1 U per µl. A standard curve is established with the *C. histolyticum* collagenase that was assayed at the following concentrations: 5 U/ml, 10 U/ml, 15 U/ml and 20 U/ml.

Incubation was at 37° C. for 6 hours. Subsequent steps were performed, as described previously for *C. histolyticum* collagenase.

Enzyme activity unit was derived from the *C. histolyticum* standard curve and expressed as *C. histolyticum* collagenase equivalent units (ChC.eqU).

Glossary of Claim Terms

Ensure substrate specificity: This term is used herein to refer to the confirmation of accuracy of the current methodology, in particular that the assay actually is detecting the specific target.

Formula I: This term is used herein to refer to the chemical structure of COOMASSIE Brilliant Blue R-250.

Native collagen fibrils: This term is used herein to refer to Type I collagen found in an animal body, where the collagen has not been denatured.

Readily observe: This term is used herein to refer to the ability to perceive a change in properties of a substrate using the naked eye.

Stably stain: This term is used herein to refer to a dye's high affinity for a particular substrate, along with ability to adhere to that substrate in a stable manner.

True collagenase activity: This term is used herein in reference to the action of an enzyme breaking the peptide bonds in native collagen within a sample. True collagenases are strictly defined as proteases capable of cleaving helical regions of collagen molecules in fibrillar form under physiological conditions of pH and temperature (D. J. Harrington, Infect. Immun. 64 (1996) 1885-1891).

All referenced publications are incorporated herein by reference in their entirety.

Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of measuring bacterial collagenase activity in a sample, comprising:
   staining native collagen fibrils with a dye at saturation level, said collagen fibrils being dry or lyophilized, said dye being capable of stably staining said collagen fibrils;
   suspending said dyed collagen fibrils in a collagenase substrate buffer;
   incubating said dyed collagen fibril suspension at about 37° C., wherein bacterial collagenase activity results in digestion of said dyed collagen fibrils into smaller, dyed collagen particulates that can be readily observed in a resulting mixture;
   filtering said mixture to retain said dyed collagen particulates, wherein said dyed collagen particulates are digested and collected in a resulting filtrate;
   extracting said dye from said filtrate to determine an amount of said digested dyed collagen particulates;
   measuring absorbance of said extracted dye to determine an amount of said digested collagen particulates;
   wherein said native fibrils are not solubilized by acid or gelled by heat, and
   wherein said native fibrils are Type I collagen found in an animal body.

2. A method as in claim 1, further comprising:
   prior to the step of staining said dried collagen fibrils, drying said native collagen fibrils, cutting said fibrils into shorter fragments, collecting said fibril fragments as dry collagen.

3. A method as in claim 1, wherein said dye is a triphenylmethane dye.

4. A method as in claim 3, wherein said triphenylmethane dye has a structure of formula I Formula I 5. A method as in claim 4, wherein the step of staining said collagen fibrils is performed using said formula I dye in a solution of acetic acid-methanol-water (1:4:5, v:v:v), at a ratio of 500 mg collagen in about 2-3 ml said acetic acid-methanol-water solution.

6. A method as in claim 1, wherein the step of measuring said absorbance of said extracted dye is performed using a plate reader or a spectrophotometer at an optimal wavelength of about 600 nm.

7. A method as in claim 1, wherein said sample includes soluble bacterial collagenase, insoluble bacterial cell-associated collagenase, or insoluble tissue-associated bacterial collagenase.

8. A method as in claim 1, wherein said sample includes a bacteria or biological sample.

9. A method as in claim 1, further comprising quantifying said bacterial collagenase activity by a concentration of said extracted dye, where said concentration is proportional to a concentration of said collagen particulates released.

10. A method as in claim 1, wherein said collagen fibrils are insoluble.

11. A method as in claim 1, wherein the step of filtering said mixture is performed through glass wool which retains any undigested collagen fibrils.

12. A method as in claim 1, wherein the step of extracting said dye from said filtrate is performed by adding an organic solvent to said filtrate and centrifuging the resulting mixture.

13. A method as in claim 12, wherein said organic solvent is detergent polysorbate 20 or a formamide.

14. A method as in claim 1, wherein a quantification of said bacterial collagenase activity is used to detect and quantify true collagenase activity in invasive pathogenic bacteria for development of drugs or vaccines to prevent invasive bacterial disease by blocking bacterial collagenase activity.

15. A method as in claim 1, wherein said collagenase substrate buffer comprises
   Tris, NaCl, and $CaCl_2$ in an approximate 5:5:1 ratio by concentration at a pH of about 7.5; or
   a phosphate buffer of NaCl, KCl, $Na_2HPO_4$, and $KH_2PO_4$ in deionized water at a pH of about 7.5.

16. A method as in claim 1, wherein said dyed collagen fibrils are further suspended in sodium azide.

17. A method as in claim 1, wherein the step of extracting said dye includes removing excess dye by rinsing with a solution of acetic acid and methanol in deionized water.

18. A method as in claim 1, further including incubating said dyed collagen fibrils with trypsin to ensure specificity.

19. A method of measuring bacterial collagenase activity in a bacterial or biological sample, wherein said sample includes soluble bacterial collagenase, insoluble bacterial cell-associated collagenase, or insoluble tissue-associated bacterial collagenase, the method comprising:
lyophilizing or drying native, insoluble collagen fibrils;
cutting said fibrils into shorter fragments;
collecting said fibril fragments as dried collagen fibrils;
staining said dried collagen fibrils with a triphenylmethane dye at saturation level in a solution of acetic acid-methanol-water (1:4:5, v:v:v), at a ratio of 500 mg collagen in about 2-3 mL said acetic acid-methanol-water solution,
wherein said native fibrils are not solubilized by acid or gelled by heat,
wherein said native fibrils are Type I collagen found in an animal body,
said triphenylmethane dye having a structure of formula I Formula I suspending said dyed collagen fibrils in sodium azide and a collagenase substrate buffer including Tris, NaCl, and $CaCl_2$) in an approximate 5:5:1 ratio by concentration at a pH of about 7.5;

incubating said dyed collagen fibril suspension at about 37° C., wherein collagenase activity results in digestion of said dyed collagen fibrils into smaller, dyed collagen particulates that can be readily observed in a resulting mixture;

filtering said mixture through glass wool to retain said dyed collagen particulates, wherein said digested dyed collagen particulates are collected in a resulting filtrate, said glass wool retaining any undigested collagen fibrils;

extracting said dye from said filtrate to determine an amount of said digested dyed collagen particulates, by adding polysorbate 20 to said filtrate, centrifuging the resulting mixture; and measuring absorbance of said extracted dye in the supernatant to determine an amount of said digested collagen particulates, wherein said measurement is taken using a plate reader or a spectrophotometer at an optimal wave length of about 600 nm;

quantifying said collagenase activity by a concentration of said extracted dye, where said concentration is proportional to a concentration of said collagen particulates released, wherein a quantification of said collagenase activity is used to detect and quantify true collagenase activity in invasive pathogenic bacteria for development of drugs or vaccines to prevent invasive bacterial disease by blocking collagenase activity;

incubating dyed collagen substrate with trypsin instead of bacterial collagenase to ensure specificity.

* * * * *